Figure 1:
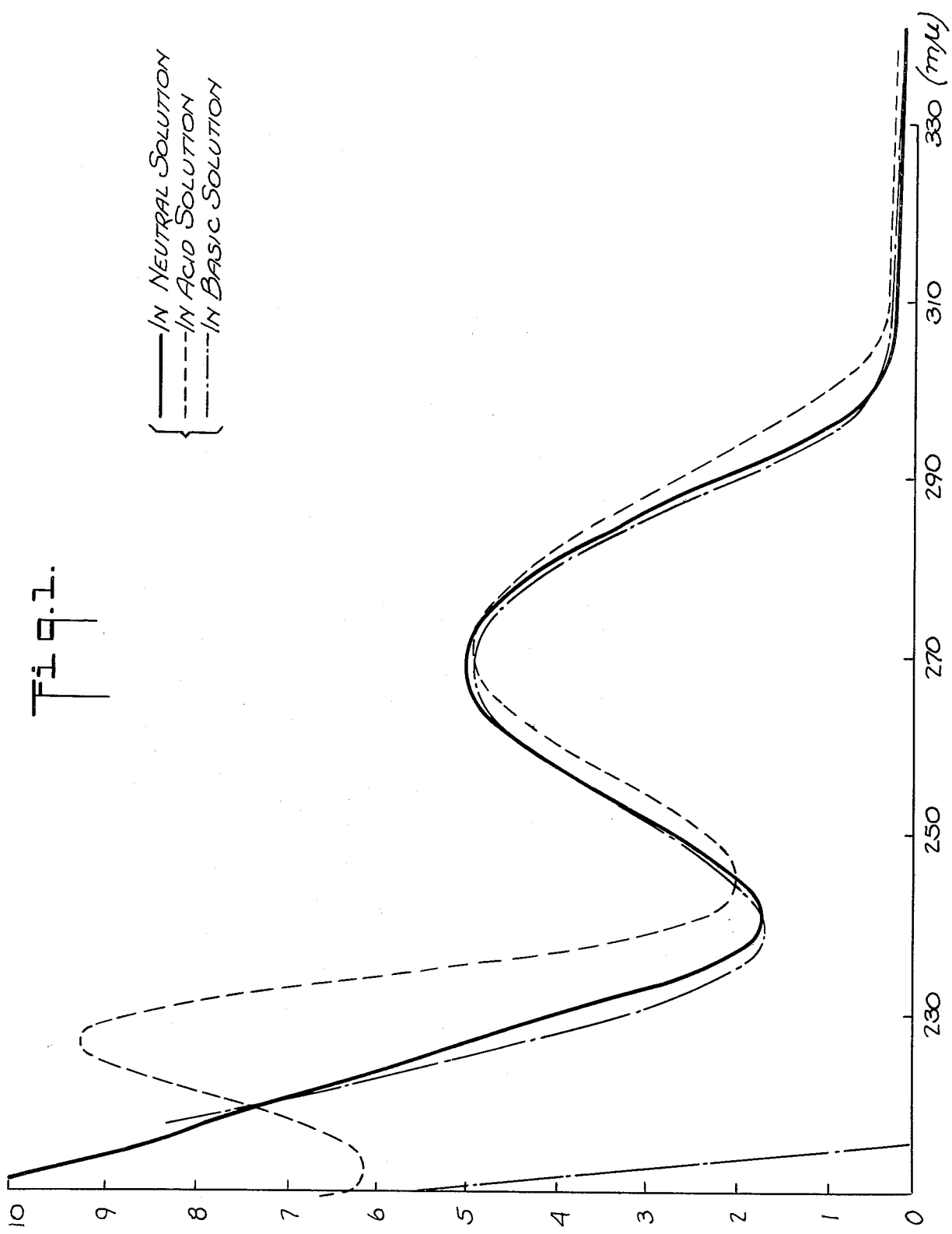

United States Patent [19]

Nara et al.

[11] 4,316,957
[45] Feb. 23, 1982

[54] PROCESS FOR THE PRODUCTION OF 7-DEAZAADENOSINE AND 7-DEAZAINOSINE

[75] Inventors: Takashi Nara, Tokyo; Ryo Okachi, Machida; Isao Kawamoto, Hiratsuka; Tomoyasu Sato; Tetsuo Oka, both of Machida, all of Japan

[73] Assignee: Abbott Laboratories, North Chicago, Ill.

[21] Appl. No.: 893,433

[22] Filed: Apr. 4, 1978

[30] Foreign Application Priority Data

Apr. 4, 1977 [JP] Japan .................................. 52-38358

[51] Int. Cl.³ .............................................. C12P 17/18
[52] U.S. Cl. .................................... 435/119; 435/88; 435/868

[58] Field of Search .................. 435/88, 128, 119, 868

[56] References Cited

U.S. PATENT DOCUMENTS 3,300,479 1/1967 Hanze ..................................... 435/88
3,454,696 7/1969 Weinstein et al. .................. 435/128

Primary Examiner—Alvin E. Tanenholtz
Attorney, Agent, or Firm—Fitzpatrick, Cella, Harper & Scinto

[57] ABSTRACT

The antibacterial compounds 7-deazaadenosine and 7-deazinosine are produced by fermentation of a new microorganism of the genus Micromonospora. At least one of the active substances is isolated from the culture medium.

6 Claims, 4 Drawing Figures

PROCESS FOR THE PRODUCTION OF 7-DEAZAADENOSINE AND 7-DEAZAINOSINE

BACKGROUND OF THE INVENTION

The present invention relates to a new process for producing the known antibiotics 7-deazaadenosine and 7-deazainosine. In the known methods, 7-deazaadenosine (also known as tubercidin) is produced by culturing an actinomycetes of the species *Streptomyces tubercidicus* [K. Anzai, et al., J. Antibiotics, A10, 201 (1957)]; and 7-deazainosine is derived from 7-deazaadenosine by chemical synthesis [Y. Mizuno, et al., J. Org. Chem., 28, 3331 (1963)].

Due to the usefulness of the foregoing compounds as antibacterial agents, new processes for the production thereof are in demand. To this end, it has now been found that 7-deazaadenosine and 7-deazainosine are produced by fermentation of microorganisms belonging to the genus Micromonospora.

SUMMARY OF THE INVENTION

In accordance with the present invention, at least one of 7-deazaadenosine and 7-deazainosine represented by the general formula:

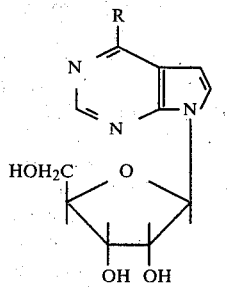

, wherein R is $NH_2$ or OH, are produced by culturing a microorganism belonging to the genus Micromonospora and having the identifying characteristics of *Micromonospora chalcea* subsp. *tubercidica* NRRL 11,107 in a nutrient medium until substantial antibacterial activity is detected in the culture liquor; and thereafter isolating at least one of said compounds from the culture liquor.

DESCRIPTION OF THE INVENTION

*Micromonospora chalcea* subsp. *tubercidica* is a novel strain isolated from a soil sample from Machida City, Tokyo, Japan. The morphological and physiological properties of the strain are as follows.

I. Morphological Characteristics

The strain grows well on natural media and poorly on synthetic media. On conventional agar medium, the strain does not form a true aerial mycelium. On agar media, to support the good growth, the substrate mycelium is granular, raised, and is orange to dark brown in color; and may have an olive to black tinge due to the good formation of spores. By microscopic observation of the cells cultured in liquid media or on agar media, it has been found that the mycelium is about 0.5 $\mu$ in diameter, well developed, straight, with long branches and septated. Sometimes a swelling-form cell is observed in the middle and on the top of the mycelium. A sporangium is not formed and spores are formed along the relatively long substrate mycelium on the top of a short sporophore branched from the mycelium in singles or clusters. The matured spores are about 1.0 $\mu$ in diameter and spherical or oval. Spore surface appears smooth by observation using an electron microscope.

II. Culture Characteristics On Various Media

Growth and color of the strain grown on various media are shown below. The color indications are given according to the classifications in the color Harmony Manual (Container Corporation of America).

The production of soluble pigment was not observed in any of the following media. Therefore, the color indicated is that of the colony-surface and reverse.

(1) Czapek's agar medium
  Growth: poor, flat, formation of green black spore-layer
  Color: Olive (1 ½ ni)
(2) Glucose-asparagine agar medium
  Growth: poor, granular
  Color: Russet Orange (4 pc)
(3) Nutrient agar medium
  Growth: poor, flat
  Color: Bright Yellow (3 na)
(4) Glycerol-asparagine agar medium
  Growth: poor, granular
  Color: Orange (4 la)
(5) Egg albumin agar medium
  Growth: poor or moderate, flat
  Color: Mustard Brown (2 pl), color of the reverse; Silver Gray (3 fe)
(6) Starch agar medium
  Growth: moderate, granular
  Color: Melon Yellow (3 ga) to Clove Brown (3 pl)
(7) Malt extract-yeast extract agar medium
  Growth: poor or moderate, granular
  Color: Light Orange (4 ia), a part shows black
(8) Oatmeal agar medium
  Growth: moderate, granular
  Color: Sun Orange (5 la) a part shows black
(9) Bennett's agar medium
  Growth: moderate or good, granular
  Color: Orange (4 la)
(10) Emerson's agar medium
  Growth: moderate or good, granular
  Color: Orange (4 la)
(11) Glucose-yeast extract agar medium
  Growth: good, raised
  Color: Deep Brown (3 pl)
(12) Hickey-Tresner's agar medium
  Growth: moderate, raised
  Color: Dark Brown (3 pn)
(13) Peptone-iron-yeast extract agar medium
  Growth: poor, flat
  Color: Orange (4 la)
(14) Tyrosine agar medium
  Growth: poor, flat
  Color: Light Melon Yellow (3 ea)

III. Physiological Properties

In the following tests, except those on the optimum temperature and action upon milk and cellulose, the observations were made after the strain is cultured at 27° C. for two weeks. The optimum temperature is determined after 5 days of culturing and the action upon milk and cellulose are observed after one month of culturing.

(1) Utilization of carbon sources: D-galactose, D-glucose, starch, D-raffinose, saccharose, D-xylose, mannose and α-melibiose are utilized but D-arabinose, glycerol, D-lactose, L-inositol, D-mannitol, and L-rhamnose are not utilized. Ability of utilization of D-fructose is weak.

(2) Liquefaction of gelatin: weak (3) Action upon milk: No coagulation is observed but a slight liquefaction is observed.

(4) Decomposition of cellulose: Slightly positive (5) Hydrolysis of starch: positive (6) Optimum pH for growth: 6.5–8.0

(7) Optimum temperature for growth: 28° C.–37° C.

(8) Reduction of nitrate: unclear (9) Formation of tyrosinase: negative

(10) Formation of melanoid pigments: negative

The strain is a mesophile, which never forms a true aerial mycelium when cultured on an agar medium, but forms a single spore on sporophore branched from the substrate mycelium. It has been found by analysis that the cell wall of this strain contains mesodiaminopimelic acid and the microbial cell contains arabinose and xylose. Accordingly, the strain is regarded as an actinomycetes belonging to the genus Micromonospora.

For identification of the species to which the strain belongs, Bergey's Manual of Determinative Bacteriology, eighth edition, was referred to for strains belonging to the genus Micromonospora which utilize α-melibiose and D-raffinose and exhibit poor growth on Czapek's agar medium. *Micromonospora chalcea* is identified as having such properties and, therefore, the instant strain is classified as belonging to *Micromonospora chalcea*.

*Micromonospora chalcea* ATCC 12452 is reported to bear black spores with a smooth surface, sessile or short sporophores, and not to produce a short length of branched and fragmented substrate mycelium. These morphological properties are also observed in the instant strain. In physiological properties, the instant strain closely parallels *Micromonospora chalcea* but actions upon gelatin, milk and cellulose are different. Specifically, the instant strain has a weaker action upon these substrates than *Micromonospora chalcea*. As for production of antibacterial substances by the species *Micromonospora chalcea*, it has been reported that the aminoglycoside antibiotic, Antibiotic No. 460 is produced by culturing *Micromonospora chalcea* subsp. *flavida* NRRL 3222 (Japanese Patent Publication No. 16153/71). On the other hand, the macrolide antibiotic, juvenimicin, is produced by culturing *Micromonospora chalcea* subsp. *izumensis* ATCC 21561 (Japanese Patent Publication No. 4514/72). However, the production of tubercidin by an organism belonging to this species has not been reported.

Based upon the foregoing, the instant strain is considered to be a new strain and has been classified as *Micromonospora chalcea* subsp. *tubercidica*. This strain has been deposited with the Fermentation Research Institute Agency of Industrial Science and Technology, Chiba City, Japan and the United States Department of Agriculture, Peoria, Ill., U.S.A. and has been accorded accession number FERM-P No. 3963 and NRRL 11107, respectively. Subcultures are freely available. Biologically pure cultures of the strain have the ability to produce, upon culturing, recoverable amounts of 7-deazaadenosine and 7-deazainosine.

As is the case with other strains of Actinomycetes, the microorganism useful in carrying out the present invention can be mutated by artifical means such as ultraviolet irradiation, X-ray irradiation and use of various mutuation inducing chemicals in known manner to enhance the production of metabolic products. Accordingly the present invention comtemplates use of such mutants insofar as they have the ability to produce 7-deazaadenosine or 7-deazainosine.

Generally, conventional methods for culturing microorganisms of the Actinomycetes may be employed in the process of the present invention. Various nutrient sources may be employed for the culture medium although natural sources are preferred. As a carbon source, glucose, starch, mannose, fructose, sucrose, molasses, and the like may be used alone or in combination. Furthermore, hydrocarbons, alcohols, organic acids, etc. may be used depending upon the ability of utilization possessed by the microorganism. Inorganic and organic nitrogen sources such as ammonium chloride, ammonium sulfate, urea, ammonium nitrate, sodium nitrate, etc. and natural nitrogen sources such as peptone, meat extract, yeast extract, dry yeast, corn steep liquor, soybean meal, casamino acid, soluble vegetable protein, etc. may be used alone or in combination. In addition, inorganic salts such as sodium chloride, potassium chloride, calcium carbonate, phosphates, may be added to the medium, if necessary. Furthermore, organic or inorganic materials capable of promoting growth of the microorganism and the production of active substances may be added to the medium.

A liquid culturing method, and especially a submerged stirring culturing method, is most suitable for the present process. It is desirable to carry out the culturing step at a temperature of 25° to 40° C. and at approximately neutral pH. Under such conditions substantial antibacterial activity is detected in the culture liquor usually after 2 to 7 days. When the antibacterial activity in the culture liquor reaches a maximum, culturing is discontinued and the desired active compounds, namely 7-deazaadenosine and/or 7-deazainosine are isolated and purified from the culture liquor after the microbial cells have been removed, such as by filtration.

Isolation and purification of the active compounds from the filtrate is carried out according to the methods usually used for the isolation and purification of microbial metabolic products from culture liquors.

Since the desired antibiotics are basic and readily soluble in water, but poorly soluble in the ordinary organic solvents, the antibiotics can be purified by the methods usually used for the purification of so-called water-soluble basic antibiotics. More specifically, the active compounds can be purified by a combination of adsorption and desorption from cation exchange resins; cellulose column chromatography; adsorption and desorption using a column of Sephadex LH-20; silica gel column chromatography; adsorption and desorption from active carbon and the like methods. For example, the culture filtrate is first adjusted to pH 4.0 with hydrochloric acid. Active carbon is added thereto and then the mixture is stirred to adsorb the active components on the active carbon. After the active carbon is thoroughly washed with water, extraction is carried out with 80% aqueous acetone. The extraction is repeated several times. The extracts are combined and concentrated under reduced pressure and then the concentrate is suspended in water-saturated n-butanol and passed through a column packed with cellulose. Elution is then carried out with the same solvent.

The fractions containing 7-deazaadenosine and 7-deazainosine are combined and concentrated under reduced pressure. The concentrate is suspended in 50% aqueous methanol and the suspension is passed through Sephadex LH-20 (product of Pharmacia Fine Chemicals Inc.). Elution is then carried out with 50% aqueous methanol. First, 7-deazainosine is eluted out, followed by 7-deazaadenosine.

Active fractions of each antibiotic are respectively combined and concentrated under reduced pressure to remove methanol. The residue is dissolved in a small amount of water and thereafter the solution is freeze-dried to obtain purified preparates of 7-deazaadenosine and 7-deazainosine.

In the purification process described above, the movement of active fractions of 7-deazaadenosine and 7-deazainosine are checked by ascending paper chromatography using Watman filter paper No. 1. Water adjusted to pH 10.0 with aqueous ammonia is used as a developer. After development is carried out at room temperature for 8 to 10 hours, spots of 7-deazaadenosine and 7-deazainosine are detected respectively near Rf 0.50 and Rf 0.62.

Physical and chemical properties of the two compounds are given in the following Table 1.

TABLE 1

Figure 2:
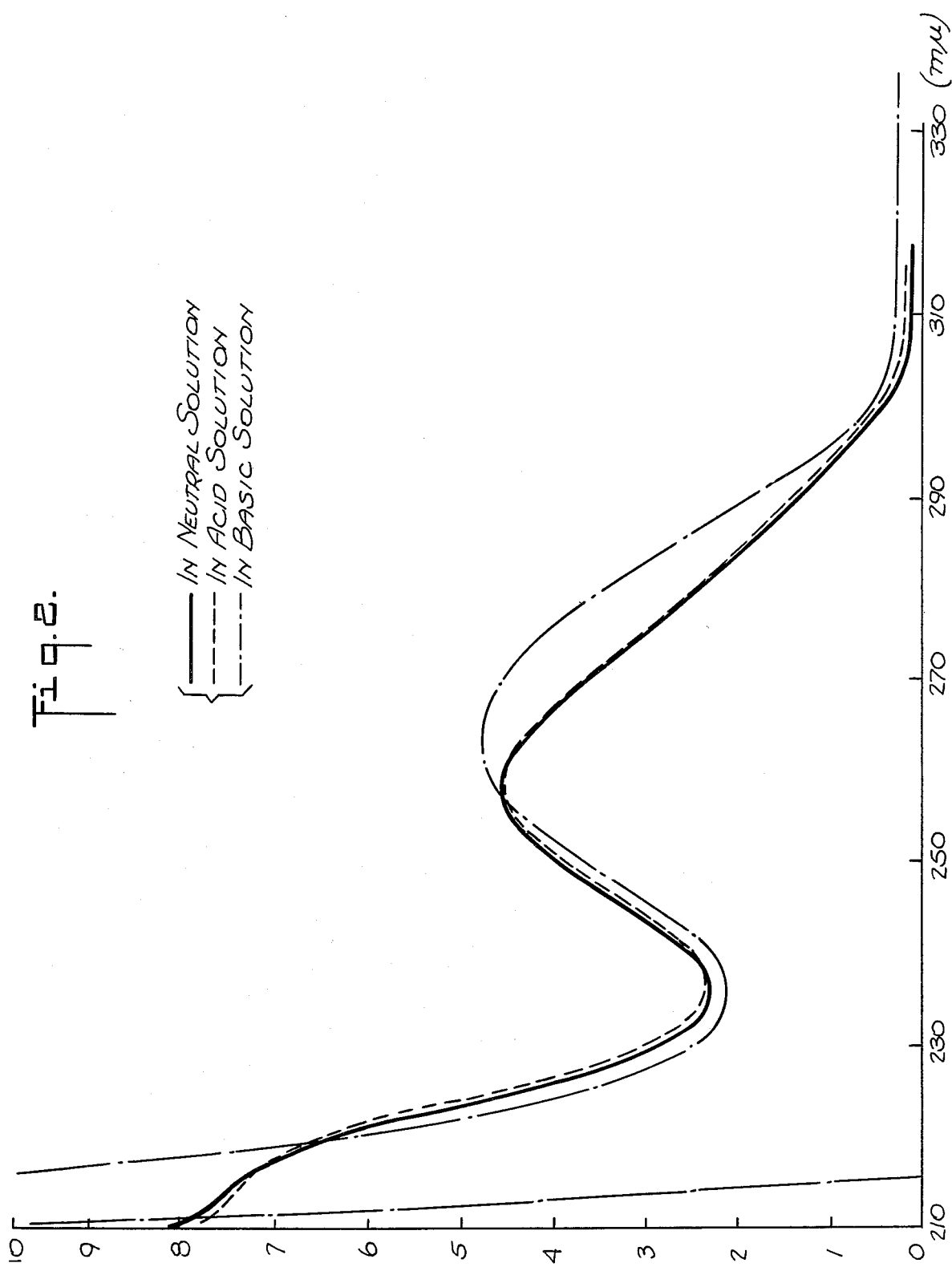
Figure 3:
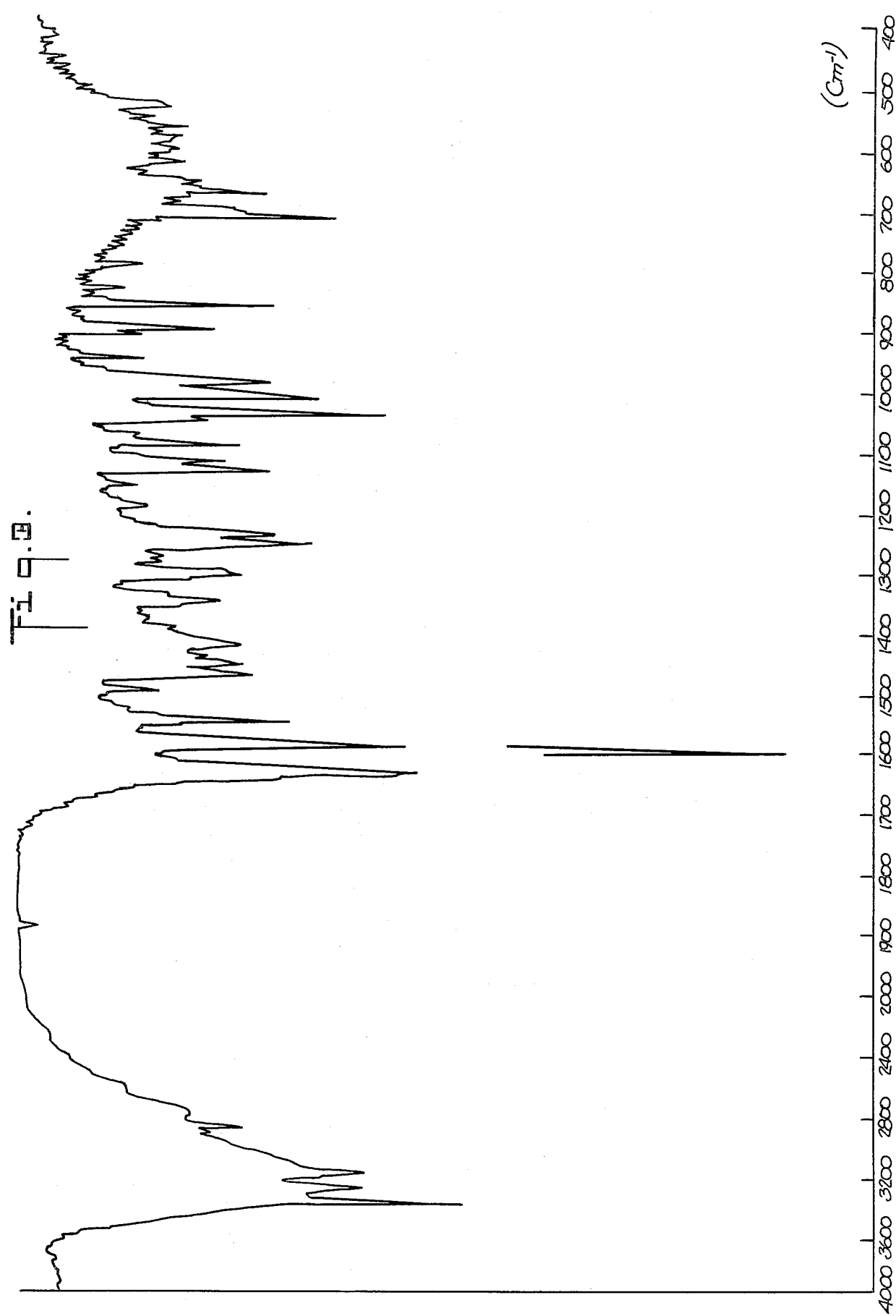
Figure 4:
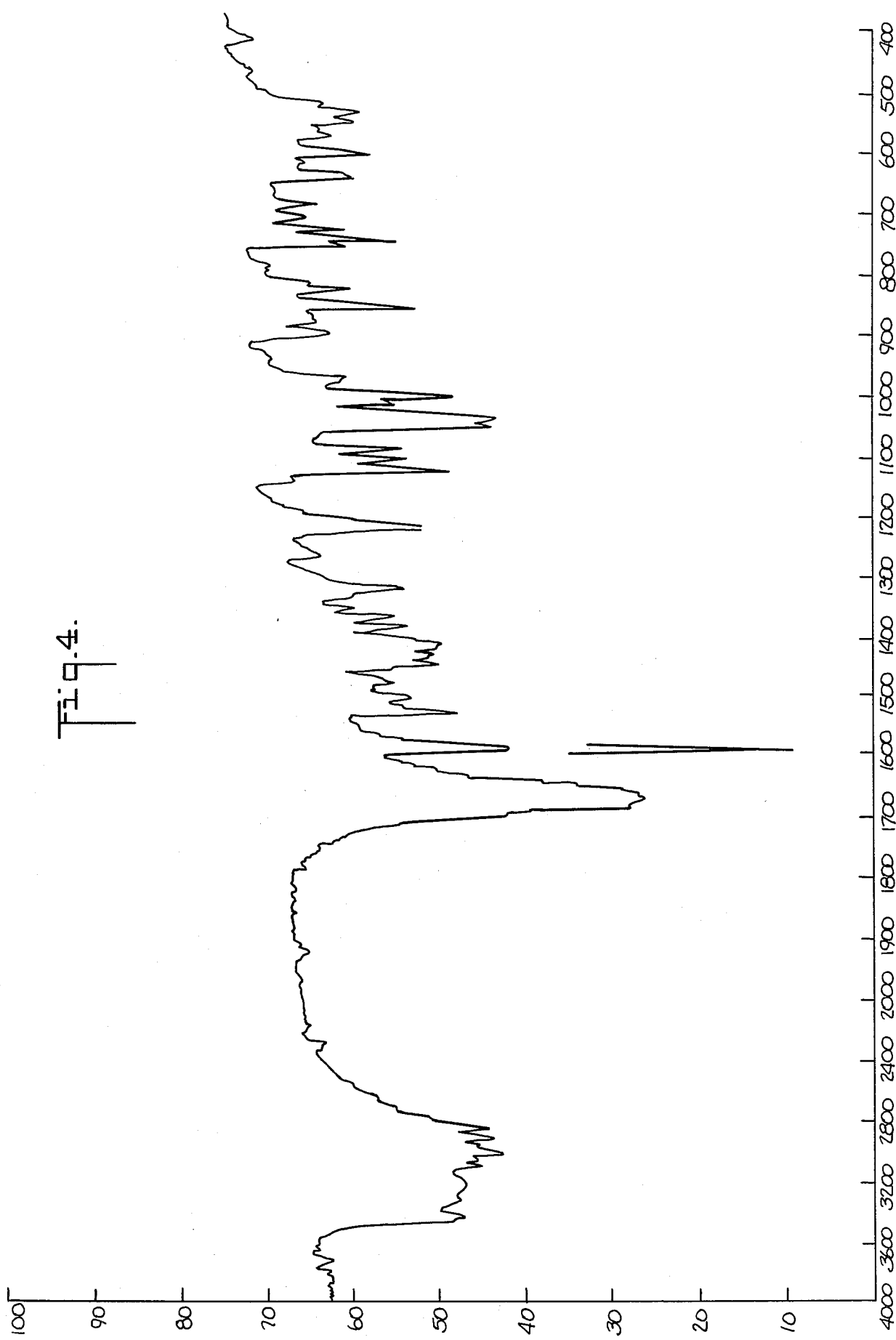

| | 7-Deazaadenosine | 7-Deazainosine |
|---|---|---|
| Elementary analysis (found) | C: 49.70%<br>H: 5.31%<br>N: 21.11% | C: 49.20%<br>H: 5.02%<br>N: 15.78% |
| Appearance | White amorphous powder | White amorphous powder |
| Molecular weight | 266 | 267 |
| Rational formula | $C_{11}H_{14}N_4O_4$ | $C_{11}H_{13}N_3O_5$ |
| Specific rotation $[\alpha]_D^{25}$ | $-67°$ (C = 0.1, $H_2O$) | $-6.5°$ (C = 0.1, $H_2O$) |
| Melting point | 247–248° C. (dec.) | 242–243° C. (dec.) |
| Solubility | Soluble in water poorly soluble in methanol insoluble in hexane, benzene and ether | Soluble in water poorly soluble in methanol insoluble in hexane, benzene and ether |
| Ultraviolet absorption spectra | FIG. 1 | FIG. 2 |
| Infrared absorption spectrum | FIG. 3 | FIG. 4 |

The Rf values of the two compounds obtained as a result of paper chromatography and thin layer chromatography using various developers are shown in the following Table 2.

TABLE 2

| | RF value | |
|---|---|---|
| Developer | 7-Deazaadenosine | 7-Deazainosine |
| I. Paper chromatography (ascending method) | | |
| n-Butanol:water(84:16, V/V) | 0.47 | 0.39 |
| Water adjusted to pH 10.0 with aqueous ammonia | 0.50 | 0.62 |
| isobutyric acid: 2.3N-aqueous ammonia (66:44, V/V) | 0.95 | 0.70 |
| 5%-sodium citrate: isoamyl-alcohol (1:1, V/V) | 0.18 | 0.14 |
| II. Thin layer chromatography (cellulose) | | |
| n-Butanol:acetic acid:water (3:1:1, V/V) | 0.80 | 0.75 |

The antibacterial spectra of 7-deazaadenosine and 7-deazainosine against various microorganisms by agar dilution method (pH 7.0) are shown in the following Table 3.

TABLE 3

| | MIC (mcg/ml) | |
|---|---|---|
| Microorganism tested | 7-Deazaadenosine | 7-Deazainosine |
| Escherichia coli KY 4271 | >100 | >100 |
| Bacillus subtilis KY 4273 | 100 | >100 |
| Mycobacterium smegmatis KY 3848 | 20 | >100 |
| Mycobacterium phlei KY 3486 | <0.045 | <0.045 |
| Pseudomonas alcaligenes KY 4656 | 10 | 40 |
| Comamonas terrigena KY 4174 | 10 | 40 |

From a comparison of the foregoing properties of the two compounds with known samples of 7-deazaadenosine and 7-deazainosine, identification of the compounds was confirmed.

Practice of certain specific embodiments of the invention is illustrated by the following representative example.

EXAMPLE 1

In this example *Micromonospora chalcea* subsp. *tubercidica* (NRRL 11107) (FERM-P No. 3963) is used as a seed strain. One loopful of the strain is inoculated into a first seed medium comprising 2 g/dl of glucose, 0.5 g/dl of peptone, 0.5 g/dl of yeast extract and 0.1 g/dl of calcium carbonate (pH 7.2 before sterilization) in a 50 ml large test tube. Culturing is carried out with shaking at 30° C. for 5 days. Then, 10 ml of the seed culture liquor is inoculated into 30 ml of a second seed medium having the same composition as that of the first medium in a 250 ml Erlenmeyer flask. The second seed culturing is carried out with shaking at 30° C. for two days. Then, 30 ml of the second seed culture liquor is inoculated into 300 ml of a third seed medium having the same composition as that of the first medium in a 2 L. Erlenmeyer flask provided with baffles. The third seed culturing is carried out with shaking at 30° C. for 2 days. Finally 900 ml of the third seed culture liquor (corresponding to the content of three flasks) is inoculated into 15 L. of a main fermentation medium in a 30 L. stainless steel jar fermenter. The main fermentation medium comprises 3 g/dl of sucrose, 1.5 g/dl of Pharmamedia brand cotton seed grounds (product of Traders Oil Mill Co.), 0.5 g/dl of meat extract, 0.5 g/dl of corn steep liquor, 0.05 g/dl of $K_2HPO_4$, 0.05 g/dl of $MgSO_4.7H_2O$, 5 mg/l of $CuSO_4.5H_2O$, 5 mg/l of $MnCl_2.4H_2O$, 5 mg/l of $ZnSO_4.7H_2O$, 1 mg/l of $CoCl_2.6H_2O$, 20 mg/l of $FeSO_4.7H_2O$ and 0.2 g/dl of $CaCO_3$ (pH 7.3 before sterilization). Culturing in the fermenter is carried out at 30° C. for 4 days with aeration and stirring (revolution: 350 r.p.m., aeration: 15 L./min.).

At the completion of fermentation, the culture liquor is adjusted to pH 4.0 with concentrated sulfuric acid and then about 1 kg of a filter aid, Radiolite No. 600 (product of Showa Kagaku Kogyo Co., Ltd.) is added thereto and the microbial cells are removed by filtration. Then, 240 g of active carbon (product of Wako Junyaku Kogyo Co., Ltd.) is added to 12 L. of the resulting filtrate and the mixture is stirred for 30 minutes. Thereafter, the active carbon is filtered, thoroughly washed with water, and then suspended in 2 L. of 80% aqueous acetone. The mixture is stirred for 15 minutes. The active carbon is filtered and the filtrate is separated. Thereafter, the active carbon is again suspended in 2 L. of 80% aqueous acetone to extract the active substances. The extraction is repeated three times so that substantially all of the active substance adsorbed on the active carbon is extracted into the aqueous acetone. The extract (6 L.) is concentrated to about 50 ml under reduced pressure.

Then 500 ml of cellulose powder (product of Avicel Funakoshi Yakuhin Co., Ltd.) is suspended in water-saturated n-butanol and the suspension is poured into a glass column so that the cellulose is uniformly packed into the column. Thereafter, 50 ml of the concentrate of the acetone extract is passed through the column. Then, elution is carried out using water-saturated n-butanol at a flow rate of about 1 ml/min.

The eluate is taken in 20 ml fractions and the activity of each fraction is determined by an ultraviolet absorption method. An active component is eluted in fraction Nos. 59–119. The active fractions are combined and a small amount of water is added thereto. Then the mixture is concentrated to about 10 ml under reduced pressure. The concentrate is suspended in 50% aqueous methanol and the suspension is passed through a glass column packed uniformly with 300 ml of Sephadex LH-20. Thereafter, elution is carried out with the same solvent at a flow rate of 1 ml/min. and the eluate is taken in 5 ml portions. 7-deazainosine is eluted out in fraction Nos. 21–28 and then 7-deazaadenosine is eluted out in fraction Nos. 39–45.

Fraction Nos. 21–28 are combined and concentrated to 5 ml under reduced pressure. Then, 2 ml of ethanol is added to the concentrate and the mixture is allowed to stand in a refrigerator to form a precipitate. The precipitate is separated and washed with methanol and dried in a desiccator to obtain 40 mg of a purified preparate of 7-deazainosine.

Fraction Nos. 39–45 are combined and concentrated to about 5 ml under reduced pressure. The concentrate is passed through a glass column packed uniformly with cellulose powder suspended in water and adjusted to pH 10.0 with concentrated aqueous ammonia. Elution is carried out with water adjusted to pH 10.0 with concentrated aqueous ammonia at a flow rate of 1 ml/min. The eluate is taken in 5 ml portions and 7-deazaadenosine is eluted in fraction Nos. 26–30. The fractions are combined and concentrated to dryness under reduced pressure. The residue is dissolved in 1 ml of hot water and the solution is allowed to stand in a refrigerator to form a precipitate. The precipitate is separated, washed with cold water and dried under reduced pressure to obtain 350 mg of a purified preparate of 7-deazaadenosine.

What is claimed is:

1. A process for the production of 7-deazaadenosine and 7-deazainosine which comprises culturing a microorganism belonging to the genus Micromonospora and having the identifying characteristics of *Micromonospora chalcea* subsp. *tubercidica* NRRL 11107 or a mutant thereof capable of producing at least one of said 7-deazaadenosine and 7-deazainosine in a nutrient medium until substantial antibacterial activity is detected in the culture liquor and thereafter isolating at least one of said 7-deazaadenosine and 7-deazainosine from said liquor.

2. A process according to claim 1 wherein 7-deazaadenosine is isolated from said culture liquor.

3. A process according to claim 1 wherein 7-deazainosine is isolated from said culture liquor.

4. A process according to claim 1 wherein said microorganism is *Micromonospora chalcea* subsp. *tubercidica* NRRL 11107.

5. A process according to claim 1 wherein said culturing step is carried out at 25° to 40° C. and approximately neutral pH for from 2 to 7 days.

6. A process for the production of 7-deazaadenosine and 7-deazainosine which comprises culturing a microorganism belonging to the genus Micromonospora and having the identifying characteristics of *Micromonospora chalcea* subsp. *tubercidica* NRRL 11107 or a mutant thereof capable of producing at least one of said 7-deazaadenosine and 7-deazainosine in a nutrient medium until substantial antibacterial activity is detected in the culture liquor and thereafter isolating in substantially pure form at least one of said 7-deazaadenosine and 7-deazainosine from said liquor.

* * * * *